United States Patent
Balschat et al.

(10) Patent No.: US 8,676,512 B2
(45) Date of Patent: Mar. 18, 2014

(54) METHOD AND DEVICE FOR DETERMINING THE TRANSMEMBRANE PRESSURE IN AN EXTRACORPOREAL BLOOD TREATMENT

(75) Inventors: Klaus Balschat, Schwebheim (DE); Alfred Gagel, Litzendorf (DE); Michael Kulz, St. Ingbert (DE); Reiner Spickermann, Wasserlosen-Burghausen (DE)

(73) Assignee: Fresenius Medical Care Deutchland GmbH, Bad Homburg (DE)

(*) Notice: Subject to any disclaimer, the term of this patent is extended or adjusted under 35 U.S.C. 154(b) by 870 days.

(21) Appl. No.: 12/809,791

(22) PCT Filed: Dec. 17, 2008

(86) PCT No.: PCT/EP2008/010727
§ 371 (c)(1),
(2), (4) Date: Jun. 21, 2010

(87) PCT Pub. No.: WO2009/080258
PCT Pub. Date: Jul. 2, 2009

(65) Prior Publication Data
US 2010/0280761 A1    Nov. 4, 2010

(30) Foreign Application Priority Data

Dec. 22, 2007 (DE) .......................... 10 2007 062 568
Mar. 7, 2008 (DE) .......................... 10 2008 013 089

(51) Int. Cl.
*A61M 1/34* (2006.01)
*G06F 19/00* (2011.01)
*G06F 17/40* (2006.01)

(52) U.S. Cl.
USPC .................... 702/19; 210/321.6; 210/321.71; 210/600; 604/6.09; 702/138; 702/187; 702/189; 708/200

(58) Field of Classification Search
USPC ........... 137/551, 557, 560; 210/85, 90, 321.6, 210/321.71, 321.72, 600, 739, 740, 767; 604/4.01, 5.01, 6.09; 702/1, 19, 127, 702/138, 187, 189; 708/100, 105, 200
IPC ..................... A61M 1/00,1/14, 1/16, 1/30, 1/34, A61M 2001/00, 2001/14, 2001/16, 2001/30, A61M 2001/301, 2001/34; B01D 61/00, B01D 61/24, 61/243, 61/246; G01D 21/00; G01L 7/00, 9/00, 11/00; G06F 11/00, 11/30, G06F 11/32, 17/00, 17/40, 19/00
See application file for complete search history.

(56) References Cited

U.S. PATENT DOCUMENTS

| | | | |
|---|---|---|---|
| 4,708,802 A | 11/1987 | Rath et al. | |
| 6,526,357 B1* | 2/2003 | Soussan et al. | ................. 702/45 |
| 6,730,233 B2 | 5/2004 | Pedrazzi | |
| 6,804,991 B2* | 10/2004 | Balschat et al. | ........... 73/40.5 R |
| 6,966,979 B2 | 11/2005 | Pedrazzi | |
| 7,131,956 B1 | 11/2006 | Pirazzoli et al. | |
| 2002/0121471 A1 | 9/2002 | Pedrazzi | |
| 2003/0136181 A1* | 7/2003 | Balschat et al. | ........... 73/40.5 R |
| 2004/0154967 A1 | 8/2004 | Pedrazzi | |
| 2004/0186410 A1 | 9/2004 | Davidner et al. | |
| 2004/0217056 A1 | 11/2004 | Muller et al. | |

FOREIGN PATENT DOCUMENTS

| | | |
|---|---|---|
| DE | 1 031 1547 | 10/2004 |
| EP | 0 212 127 | 3/1987 |
| EP | 1 604 699 | 12/2005 |
| EP | 1 655 043 | 5/2006 |
| JP | 2-68069 A * | 3/1990 |
| JP | 2003-116985 | 4/2003 |
| WO | WO 03/028860 | 4/2003 |
| WO | WO 2004/082743 | 9/2004 |
| WO | WO 06/011009 | 2/2006 |

OTHER PUBLICATIONS

Polaschegg, H.D., "Methods and History of Ultrafiltration Control in Hemodialysis", Aktuelle Nephrologie, ISSN, 0341-437X, 18(1985) Heft 1, pp. 135-48. (English-language abstract enclosed).
PCT International Search Report for PCT/EP08/010727 mailed on May 8, 2009.

* cited by examiner

Primary Examiner — Edward Cosimano
(74) Attorney, Agent, or Firm — Kenyon and Kenyon LLP

(57) ABSTRACT

A method and device are provided for determining the transmembrane pressure during an extracorporeal blood treatment in which blood flows at a defined blood flow rate through an arterial blood conduit of an extracorporeal blood circuit into the inlet of a first chamber of a dialyzer, which is divided by a semipermeable membrane into the first chamber and a second chamber, and flows through a venous blood conduit from the outlet of the first chamber of the dialyzer, while dialysis liquid flows through a dialysis liquid supply conduit into the inlet of the second chamber of the dialyzer and flows through a dialaysis liquid discharge conduit from the outlet of the second chamber of the dialyzer. The method and the device for determining the transmembrane pressure are such that the pressure on the blood side and on the dialysis liquid side of the dialyzer is measured with relatively little technical outlay, specifically with fewer than four pressure sensors, and a preliminary uncorrected value is calculated for the transmembrane pressure and is thereafter corrected by a correction variable that is dependent on a variable correlating with the viscosity of the blood.

20 Claims, 2 Drawing Sheets

Legend:
1 Dialyzer
2 Membrane
3 First/Blood Chamber
4 Second/Dialyzing Fluid Chamber
8, 13, 14, 16 Pump
9 Dialyzing Fluid Source
12 Drain
17 Filter
18 Central Control and Computing Unit
19 Computing Unit
19A Memory
20, 21, 22 Pressure Sensors
23 Measuring Unit

30 Measure pressure on blood side at inlet or outlet of first chamber and on dialyzing fluid side at inlet and/or outlet of second chamber
OR
Measure pressure on blood side at inlet and/or outlet of first chamber and on dialyzing fluid side at inlet or outlet of second chamber
31

Determine a variable correlating with blood viscosity
32

Determine a correcting quantity, dependent on the variable correlating with blood viscosity, for the transmembrane pressure
33

Calculate the transmembrane pressure based on the measured pressures and the correcting quantity
34

FIG. 2

METHOD AND DEVICE FOR DETERMINING THE TRANSMEMBRANE PRESSURE IN AN EXTRACORPOREAL BLOOD TREATMENT

FIELD OF THE INVENTION

The present invention relates to a method for determining the transmembrane pressure during an extracorporeal blood treatment, in which blood flows at a specific blood flow rate via an arterial blood supply line of an extracorporeal blood circuit into the inlet of a first chamber of a dialyzer divided by a semipermeable membrane into the first chamber and a second chamber and flows via a venous blood return line from the outlet of the first chamber of the dialyzer, whilst dialyzing fluid flows via a dialyzing fluid supply line into the inlet of the second chamber of the dialyzer and flows via a dialyzing fluid discharge line out of the outlet of the second chamber of the dialyzer, fluid being withdrawn from the blood at a specific flow rate via the membrane of the dialyzer. Moreover, the present invention relates to an extracorporeal blood treatment in which the transmembrane pressure is determined. Furthermore, the present invention relates to a device for determining the transmembrane pressure for a blood treatment apparatus for performing an extracorporeal blood treatment and an extracorporeal blood treatment apparatus with a device for determining the transmembrane pressure.

BACKGROUND

Various methods for extracorporeal blood treatment or cleaning are used for the purpose of removing substances usually eliminated with urine and for the purpose of withdrawing fluid. In the case of hemodialysis, the patient's blood is cleaned outside the body in a dialyzer. The dialyzer has a blood chamber and a dialyzing fluid chamber, which are separated by a semipermeable membrane. During the treatment, the patient's blood flows through the blood chamber. In order to clean the blood effectively from substances usually eliminated with urine, fresh dialyzing fluid continuously flows through the dialyzing fluid chamber.

Whereas the transport of the smaller molecular-weight substances through the membrane of the dialyzer is essentially determined by the concentration differences (diffusion) between the dialyzing fluid and the blood in the case of hemodialysis (HD), substances dissolved in the plasma water, in particular higher molecular-weight substances, are effectively removed by a high fluidic flow (convection) through the membrane of the dialyzer in the case of hemofiltration (HF). In hemofiltration, the dialyzer acts as a filter, which is therefore referred to in the following as a dialyzer. Hemodiafiltration (HDF) is a combination of the two methods.

In the case of hemo(dia)filtration (HDF), a part of the serum withdrawn via the membrane of the dialyzer is replaced by a sterile substitution fluid, which is supplied to the extracorporeal blood circuit upstream and/or downstream of the dialyzer. The supply of substitution fluid upstream of the dialyzer is referred to as pre-dilution and the supply downstream of the dialyzer as post-dilution.

In an extracorporeal blood treatment, the ultrafiltration rate (UF rate) is of interest, which is a measure of the amount of fluid withdrawn from the patient within a time interval. The ultrafiltration rate is dependent on transmembrane pressure TMP in the extracorporeal blood treatment, the ultrafiltration rate increasing with increasing transmembrane pressure.

Transmembrane pressure TMP is defined as the pressure difference between the mean blood-side pressure and the mean dialysate-side pressure on the dialyzer. In principle, four pressure measurements are required for an exact determination of the transmembrane pressure, the pressure being measured at the inlet and outlet of the blood chamber and inlet and outlet of the dialyzing fluid chamber of the dialyzer. For this purpose, a pressure sensor is required in each case at the blood-side inlet and outlet and at the dialysate-side inlet and outlet of the dialyzer.

In practice, however, the measurement of the transmembrane pressure by means of four pressure sensors proves to be relatively expensive. For reasons of technical simplification, therefore, the determination of the transmembrane pressure by means of four pressure sensors is generally refrained from in practice.

For the determination of the transmembrane pressure, it is known to determine the pressure solely by means of two pressure sensors, whereof one pressure sensor is disposed on the blood side and the other pressure sensor on the dialysate side. For reasons of handling and cost, it is proposed, for example in the article by H. D. Polaschegg "Methods and history of ultrafiltration control in haemodialysis" (Aktuelle Nephrologie, vol. 1/1985, page 135 and following), to restrict the measurement to the venous backflow pressure and the pressure at the dialyzing fluid outlet.

Apart from the determination of the transmembrane pressure by means of two pressure sensors, the determination of the membrane pressure by means of three pressure sensors is also known. For the determination of the transmembrane pressure, European patent application publication EP 0 212 127, for example, proposes measuring the pressure in the dialyzing fluid supply line and discharge line and the pressure in the blood return line, in particular the drip chamber disposed in the blood return line, and calculating the transmembrane pressure on the basis of the measured pressures. The calculated transmembrane pressure is compared with a predetermined setpoint value for the mean transmembrane pressure, in order to adjust the dialyzing fluid pump disposed in the dialyzing fluid discharge line. The suction pump on the dialyzing fluid side is regulated in such a way that the transmembrane pressure in the dialyzer is kept at the setpoint value.

In practice, the determination of the transmembrane pressure on the basis of only two or three pressure measurements, whereof one pressure measurement takes place on the blood side and the other measurement on the dialysate side in each case, has been considered to be sufficiently accurate. The inventors have found, however, that under certain treatment conditions limiting factors have to be placed on the determination of the transmembrane pressure with a high degree of accuracy.

A goal of the present invention is to provide a method for determining the transmembrane pressure in an extracorporeal blood treatment, which on the one hand requires only a relatively small technical outlay for the measurement and on the other hand guarantees a high degree of accuracy under all treatment conditions.

Moreover, it is a goal of the present invention to provide a device for determining the transmembrane pressure for an extracorporeal blood treatment apparatus, which permits a determination of the transmembrane pressure with a high degree of accuracy with less than four pressure sensors under all treatment conditions.

Further goals of the present invention are to provide a method for extracorporeal blood treatment and an extracorporeal blood treatment apparatus, wherein the determination of the transmembrane pressure takes place with a high degree of accuracy with a relatively low technical outlay.

SUMMARY

The method according to example embodiments of the present invention and the device according to example embodiments of the present invention for determining the transmembrane pressure are based on the fact that the pressure on the blood side and dialyzing fluid side of the dialyzer is measured with less than four pressure sensors with a relatively low technical outlay and a preliminary uncorrected value for the transmembrane pressure is calculated, which is then corrected with a correcting quantity which is dependent on a variable correlating with the viscosity of the blood. Consequently, a variable correlating with the viscosity of the blood, in particular the hematocrit of the blood, is taken into account in the determination of the transmembrane pressure.

The inventors have found that, especially in the case of marked thickening or thinning of the blood, such as can occur during hemodiafiltration treatment or hemofiltration treatment, deviations can occur between the actual transmembrane pressure and the value for the transmembrane pressure which results from the measurement of the pressure at less than four measuring points, for example in the case of a measurement of the pressure only at the inlet or outlet, but not at the inlet and outlet of the respective chambers of the dialyzer.

With the method according to the invention, the determination of the transmembrane pressure is also particularly accurate when erythropoietin (EPO) is administered to the patient, as a result of which the hematocrit increases and the viscosity of the blood rises.

In a preferred example embodiment of the method according to the present invention and the device according to the present invention, the pressure on the blood side is measured in the blood return line at the outlet of the first chamber of the dialyzer, whilst on the dialyzing fluid side the pressure is measured in the dialyzing fluid supply line at the inlet of the second chamber and in the dialyzing fluid discharge line at the outlet of the second chamber of the dialyzer. It is therefore not necessary to measure the pressure on the blood side in the blood supply line at the inlet of the first chamber of the dialyzer, so that the pressure measurement can take place with only three pressure sensors.

It is, however, also possible that, on the blood side, the pressure is measured not at the outlet, but at the inlet of the first chamber of the dialyzer. Likewise, it is possible that the pressure on the blood side is measured both at the inlet and outlet of the first chamber of the dialyzer, whilst the pressure on the dialyzing fluid side is measured only either at the inlet or at the outlet of the second chamber of the dialyzer. The decisive factor is that at least one pressure measurement takes place both on the blood side and the dialyzing fluid side of the dialyzer.

When mention is made of a measurement of the pressure at the inlet or outlet of one of the two chambers of the dialyzer, this does not necessarily have to be understood to mean that the measurement has to take place directly at the point at which the lines are connected to the dialyzer. On the contrary, it is also possible to carry out the measurement upstream or downstream of the inlet or outlet, whereby it is to be assumed that the pressure increase or pressure decrease between the actual measuring point and the inlet or outlet of the respective chamber of the dialyzer is small.

The correcting quantity for the transmembrane pressure is preferably a parameter characteristic of the flow resistance of the dialyzer in the longitudinal direction, said parameter in turn being dependent on a parameter correlating with the viscosity of the blood, in particular on the hematocrit.

It has been shown that the deviations between the transmembrane pressure that is calculated on the basis of a measurement with less than four pressure sensors and the actual transmembrane pressure increases with increasing flow resistance of the dialyzer in the longitudinal direction. Since, in the determination of the transmembrane pressure by the method according to the present invention and the device according to the present invention, the flow resistance of the dialyzer in the longitudinal direction is taken into account, the actual transmembrane pressure can be calculated with a high degree of accuracy.

The flow resistance of the dialyzer in the longitudinal direction, which is dependent on a parameter correlating with the viscosity of the blood, in particular the hematocrit, can in principle be calculated at the start of the blood treatment or during the blood treatment.

A particularly preferred embodiment of the invention provides for a continuous determination of the parameter correlating with the viscosity of the blood, in particular the hematocrit, during the blood treatment, whereby the hematocrit is measured on-line.

The dependence of the longitudinal resistance of the dialyzer on the variable correlating with the viscosity of the blood, in particular on the hematocrit, is preferably described by a polynomial approach, the parameters of which are determined from individual measurement data for each relevant type of dialyzer on the assumption of a pre- or post-dilution.

The inventors have found that the flow resistance in the longitudinal direction of the dialyzer is essentially dependent on the design of the dialyzer, which is characterized by a specific membrane area or length and a specific diameter of the capillaries, on the type of treatment, for example an HD treatment or H(D)F treatment with pre-dilution or post-dilution, on the substitution rate and on the ultrafiltration rate and the blood constituents. In a preferred embodiment of the invention, therefore, the aforementioned quantities are taken into account in the polynomial approach for the determination of the longitudinal resistance of the dialyzer.

The correcting quantity for the transmembrane pressure is preferably determined on the basis of the product of the parameter characteristic of the flow resistance in the longitudinal direction of the dialyzer and the blood flow rate in the extracorporeal blood circuit. The correcting quantity is therefore also dependent on the blood flow.

The method according to the present invention and the device according to the present invention therefore proceed on the basis that the deviations between the transmembrane pressure calculated on the basis of the measured pressures and the actual transmembrane pressure increase with increasing viscosity of the blood and with increasing blood flow.

The device according to the present invention for determining the transmembrane pressure, which is determined for a blood treatment apparatus for performing an extracorporeal blood treatment, comprises means for measuring the pressure on the blood side and the dialyzing fluid side and means for calculating the transmembrane pressure taking account of the correcting quantity. The means for measuring the pressure on the blood side and the dialyzing fluid side of the dialyzer comprise, in a preferred example embodiment, means for measuring the pressure in the blood return line at the outlet of the first chamber of the dialyzer as well as means for measuring the pressure in the dialyzing fluid supply and return line at the inlet and outlet of the second chamber of the dialyzer.

Means for measuring the pressure in the blood supply line at the inlet of the first chamber of the dialyzer are not therefore required.

The means for measuring the pressure can be conventional pressure sensors, which are in any case present in the case of the known blood treatment apparatuses. The means for calculating the transmembrane pressure can be a conventional microprocessor or suchlike, which is also in any case present in the known blood treatment apparatuses.

An example embodiment of the method according to the present invention and the device according to the present invention will be described in detail below by reference to the appended figures.

BRIEF DESCRIPTION OF THE DRAWINGS

FIG. 2 shows a method for determining the transmembrane pressure in a greatly simplified schematic representation.

DETAILED DESCRIPTION

Figure 1:
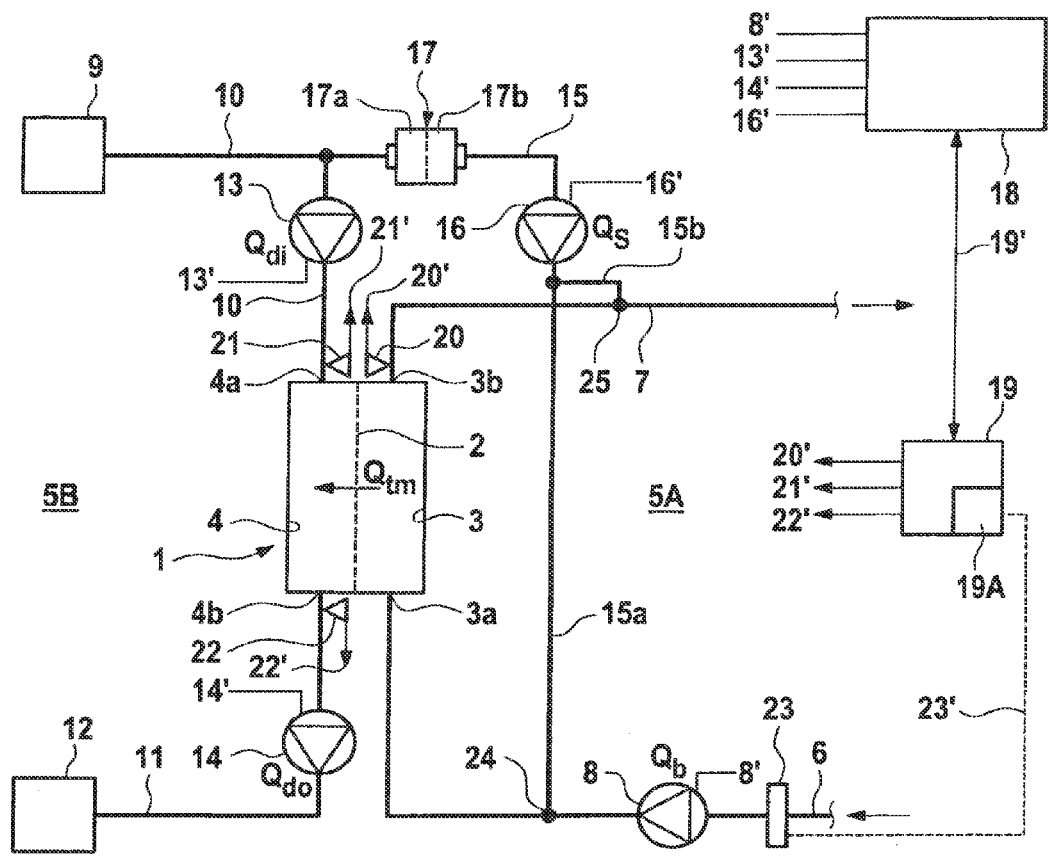
FIG. 1 shows only the main components of a blood treatment apparatus for an extracorporeal blood treatment together with a device for determining the transmembrane pressure in a greatly simplified schematic representation.

The device according to the invention for measuring the transmembrane pressure can be a component of a conventional blood treatment apparatus or a separate device unit which cooperates with the blood treatment apparatus.

The present blood treatment apparatus is a hemo(dia)filtration apparatus, which comprises a dialyzer 1, which is divided by a semipermeable membrane 2 into a first chamber 3 through which blood flows and which will be referred to in the following as a blood chamber, and a second chamber 4 through which dialyzing fluid flows which will be referred to as a dialyzing fluid chamber. First chamber 3 is incorporated into an extracorporeal blood circuit 5A, whilst second chamber 4 is incorporated into dialyzing fluid system 5B of the hemo(dia)filtration apparatus.

Extracorporeal blood circuit 5A comprises an arterial blood supply line 6 which leads to inlet 3a of chamber 3, and a venous blood return line 7 which departs from outlet 3b of blood chamber 3 of dialyzer 1. The patient's blood is conveyed through blood chamber 3 of dialyzer 1 by an arterial blood pump 8, in particular a roller pump, which is disposed on arterial blood supply line 6. The blood pump delivers blood at a specific blood flow rate $Q_b$ to blood chamber 3 of the dialyzer. In order to eliminate air bubbles, an air separator (drip chamber) can be incorporated into the arterial and venous blood line.

Blood lines 6, 7 of the blood treatment apparatus are tube lines which are placed into the roller pumps for one-off use. In principle, therefore, the tube lines may not be a component of the blood treatment apparatus. In principle, the dialyzer may also not be a component of the blood treatment apparatus, but rather is connected for one-off use to the tube lines.

The fresh dialyzing fluid is made available in a dialyzing fluid source 9. A dialyzing fluid supply line 10 leads from dialyzing fluid source 9 to inlet 4a of dialyzing fluid chamber 4 of dialyzer 1. A dialyzing fluid discharge line 11 leads from outlet 4b of dialyzing fluid chamber 4 to a drain 12. A first dialyzing fluid pump 13 is incorporated into dialyzing fluid supply line 10 and a second dialyzing fluid pump 14 is incorporated into dialyzing fluid discharge line 11. First dialyzing fluid pump 13 delivers dialyzing fluid from the dialyzing fluid source at a specific dialyzing fluid supply rate $Q_{di}$ to inlet 4a of dialyzing fluid chamber 4, whilst second dialyzing fluid pump 14 delivers dialyzing fluid at a specific dialyzing fluid discharge rate $Q_{do}$ from outlet 4b of dialyzing fluid chamber 4 to drain 12.

During the dialysis treatment, dialyzing fluid from dialyzing fluid system 5B can be fed as a substitution fluid via a substitution fluid line 15 to extracorporeal circuit 5A, which branches off from dialyzing fluid supply line 10 upstream of first dialyzing fluid pump 13.

Substitution fluid line 15 comprises two line sections 15a and 15b, whereof one line section 15a leads to arterial blood line 6 and the other line section 15b leads to venous blood line 7.

The substitution fluid is delivered by means of a substituate pump 16, in particular a roller pump, into which substitution fluid line 15 is inserted. A sterile filter 17 divided into two chambers 17a, 17b is incorporated into substitution fluid line 15 upstream of the substituate pump. The substituate pump together with the accompanying lines and the sterile filter form the substitution device of the dialysis apparatus. For the clamping of the two line sections 15a, 15b of substitution fluid line 15, shut-off elements, for example hose clamps, can be provided, which however are not represented for the sake of greater clarity.

Blood pump 8, first and second dialyzing fluid pump 13 and 14 and substituate pump 16 are connected via control lines 8', 13', 14', 16' to a central control and computing unit 18, from which the pumps are controlled taking account of the preselected treatment parameters. Control and computing unit 18 also controls the shut-off elements (not shown), in order to perform the blood treatment with pre-dilution or post-dilution.

For the operation of the hemo(dia)filtration apparatus as a hemodialysis apparatus, blood pump 8 and first and second dialyzing fluid pumps 13 and 14 are operated, dialyzing fluid flowing through dialyzing fluid chamber 4 of dialyzer 1. For the operation of the hemo(dia)filtration apparatus as a hemodiafiltration apparatus, substituate pump 16 is operated, so that sterile dialyzing fluid as a substitution fluid flows via sterile filter 17 optionally to arterial supply point 24 downstream of blood pump 8 and upstream of blood chamber 3 (pre-dilution) or to venous supply point 25 downstream of the blood chamber (post-dilution). In principle, however, an operation of the hemo(dia)filtration apparatus is also possible solely as a hemofiltration apparatus, if first dialyzing fluid pump 13 is not operated and the supply of dialyzing fluid into the dialyzing fluid chamber of the dialyzer is thus interrupted.

The processing of the treatment parameters characteristic of the blood treatment takes place in central control and computing unit 18 of the blood treatment apparatus. These characteristic variables can either be inputted by the operator of the machine, be measured during the treatment and/or be calculated from measured and/or preselected variables. In the following, it is assumed that all of the variables of relevance here are made available by the central control and computing unit, since they are inputted by the operator via a keyboard (not shown) and/or measured by measuring units (not shown) and/or calculated from the inputted and/or measured variables.

The device according to the invention for determining the transmembrane pressure can form an independent module or component of central control and computing unit 18 of the blood treatment apparatus. In the present example embodiment, the relevant components of the device for determining the transmembrane pressure form a separate module which will be described in detail below.

The device for determining the transmembrane pressure comprises a central computing unit 19, for example a microprocessor, which may also be the microprocessor which is provided in central control and computing unit 18 of the treatment apparatus. Moreover, the device for determining the transmembrane pressure can comprise a total of three pressure sensors 20, 21, 22, whereof the first pressure sensor measures the pressure at outlet 3b of first chamber 3 of dialyzer 1, second pressure sensor 21 measures the pressure at inlet 4a of second chamber 4 and pressure sensor 22 measures the pressure at outlet 4b of sec- and chamber 4 of dialyzer 1. These pressure sensors do not have to be disposed directly at the inlet and outlet of the dialyzer. The decisive factor is that the pressure is measured with sufficient accuracy at the blood-side outlet and at the dialysate-side inlet and outlet of the dialyzer.

Computing unit 19 receives the measured values of pressure sensors 20, 21, 22 via data lines 20', 21' and 22'. Moreover, computing unit 19 communicates via a further data line 19' with central control and computing unit 18 of the blood treatment apparatus in order to receive the variables of relevance here, which are inputted by the operator and/or are measured by sensors (not shown) and/or are calculated.

In a preferred embodiment, the device for determining the transmembrane pressure also comprises a measuring unit 23 for measuring the hematocrit of the blood flowing in extra-corporeal blood circuit 5A, which can change in the course of the extracorporeal blood treatment. On account of the ultrafiltration, the hematocrit generally increases during the blood flow treatment. Computing unit 19 is connected via a data line 23' to measuring unit 23 for determining the hematocrit. Measuring units for determining the hematocrit are known to the person skilled in the art from the prior art.

The theoretical principles of the determination of the transmembrane pressure and the device according to the invention for determining the transmembrane pressure and the method according to the invention, according to which the device for determining the transmembrane pressure works, are described in detail below.

Four pressure sensors are in principle required for the exact determination of mean transmembrane pressure TMP. After the measurement of the pressure at blood-side inlet $P_{b,out}$, the pressure at blood-side outlet $P_{b,out}$, the pressure at dialysate-side inlet $P_{d,in}$ and the pressure at dialysate-side outlet $P_{d,out}$, transmembrane pressure $P_{TM}$ (TMP) can be calculated according to the following equation $$TMP = P_{TM} = \frac{P_{b,in} + P_{b,out}}{2} - \frac{P_{d,in} + P_{d,out}}{2} \quad (1)$$

where
$P_{TM}$ transmembrane pressure TMP
$P_{b,in}$ pressure at the blood-side inlet of the dialyzer
$P_{b,out}$ pressure at the blood-side outlet of the dialyzer (=venous pressure $P_{ven}$)
$P_{d,in}$ pressure at the dialysate-side inlet of the dialyzer
$P_{d,out}$ pressure at the dialysate-side outlet of the dialyzer In the present example embodiment, however, the pressure is measured not by means of four pressure sensors at the aforementioned measuring points, but only by means of three pressure sensors 20, 21, 22, which measure pressure $P_{b,out}$ at blood-side outlet 3b of blood chamber 3 of dialyzer 1, $P_{d,in}$ at dialysate-side inlet 4a and $P_{d,out}$ at dialysate-side outlet 4b of dialyzing fluid chamber 4 of dialyzer 1.

The differences between the determination of the transmembrane pressure on the basis of a measurement at three measuring points and a measurement at four measuring points result from pressure drop $\Delta P_b$ on the blood side of the dialyzer, which increases with increasing viscosity of the blood, increasing blood flow $Q_b$ and smaller capillary diameter with identical membrane area. Smaller or larger differences between the two measurements may result according to the possible combinations of the boundary conditions.

Moreover, the viscosity of the blood in the dialyzer can be changed by the treatment process. In the case of an H(D)F treatment, for example, the mean blood viscosity in the dialyzer (filter) diminishes in the case of pre-dilution, whereas the mean blood viscosity increases in the case of post-dilution. Post-dilution therefore leads to greater differences in the two measurements. This can be traced back to the different transmembrane flow via the membrane of the dialyzer, which is withdrawn from blood flow $Q_b$. Total transmembrane flow $Q_{tm}=Q_{uf}+Q_{sub}$ is composed of ultrafiltration rate $Q_{uf}$ and substitution rate $Q_{sub}$. In practice, however, substitution rate $Q_{uf}$ can often be neglected.

Example embodiments of the present invention are based on calculating transmembrane pressure $P_{TM3}$ on the basis of the pressure measured with three pressure sensors 20, 21, 22 and determining a correcting quantity for the calculated transmembrane pressure, in order to ascertain actual transmembrane pressure $P_{TM}$=TMP.

By transforming equation (1), the following results:

$$P_{TM} = P_{b,out} - \frac{P_{d,in} + P_{d,out}}{2} + \frac{P_{b,in} + P_{b,out}}{2} \quad (2)$$

Uncorrected transmembrane pressure $P_{TM3}$ is contained therein:

$$P_{TM3} = P_{b,out} - \frac{P_{d,in} + P_{d,out}}{2} \quad (3)$$

The correction term results from a comparison of equation (3) and equation (2) from the last term of equation (2). It reflects the blood-side pressure drop on the longitudinal side of blood chamber 3 of dialyzer 1:

$$\frac{P_{b,in} - P_{b,out}}{2} = \frac{\Delta P_b}{2} \quad (4)$$

where:
$\Delta P_b$ pressure drop on the longitudinal side of the dialyzer (blood side).

The pressure drop on the blood side of the dialyzer chiefly depends on blood flow $Q_b$. This relationship can generally be described by a polynomial approach $$\Delta P_b = \sum_{i=0}^{n} c_i * Q_b^i \quad (5)$$

As a rule, linear dependences between pressure drop $\Delta P_b$ and blood flow $Q_b$ result with sufficient accuracy in practice. The pressure drop on the blood side $\Delta P_b$ can thus be split up into a flow resistance $R_b$ in the longitudinal direction of the dialyzer, which is independent of blood flow $Q_b$, and current blood flow $Q_b$. The following thus results:

$$P_{TM} = P_{TM3} + \frac{1}{2} * R_b * Q_b \quad (6)$$

where:
$R_b$ longitudinal resistance of the dialyzer on the blood side
$Q_b$ blood flow In the present example embodiment, a polynomial approach with parameters $\alpha_0, \alpha_1, \alpha_2, \alpha_3, \alpha_4 \ldots$ is used to calculate flow resistance $R_b$ in the longitudinal direction of blood chamber 3 of dialyzer 1. An example of a possible polynomial approach is:

$$R_b(Hkt, Q_{tm}) = a_0 + a_1 * Hkt + a_2 * \frac{Q_{tm}}{Q_{tm,max}} + \quad (7)$$
$$a_3 * Hkt * \frac{Q_{tm}}{Q_{tm,max}} + a_4 * \left(Hkt * \frac{Q_{tm}}{Q_{tm,max}}\right)^4$$

$Q_{tm,max}$ can be determined for the case of post-dilution or pre-dilution as follows:

$$Q_{tm,Post,max} = Q_b * (1 - Hkt) * \left(1 - k * \frac{TP}{100}\right) \quad (8)$$

or $$Q_{tm,Prae,max} = Q_{tm,Post,max} \left(k * \frac{TP}{100 \text{ g/dl}}\right) \quad (9)$$

where k is a factor, for example k=7, and where:
Hkt hematocrit [0.10 . . . 0.69]
TP total protein content [5.0 . . . 9.0 g/dl]
$Q_{tm}$ current flow rate via the dialyzer membrane [ml/min]; where: $Q_{tm} = Q_{sub} + Q_{uf}$
$Q_{sub}$ substitution rate [ml/min];
$Q_{uf}$ ultrafiltration rate [ml/min];
$Q_{tm,max}$ maximum flow rate [ml/min] where
post-dilution: $Q_{tm,post,max}$ according to equation (8), or where
pre-dilution: $Q_{tm,pre,max}$ according to equation (9)

Instead of the polynomial approach according to equation (7), a general approach is also possible, which takes account of higher powers for hematocrit Hkt, for transmembrane flow $Q_{tm}$ and the product of hematocrit and transmembrane flow.

$$R_b(Hkt, Q_{tm}) = \quad (10)$$
$$\sum_{i=0}^{n} b_{1,i} * Hkt^i + \sum_{j=1}^{m} b_{2,j} * \left(\frac{Q_{tm}}{Q_{tm,max}}\right)^j + \sum_{k=1}^{p} b_{3,k} * \left(Hkt * \frac{Q_{tm}}{Q_{tm,max}}\right)^k$$

The device according to example embodiments of the present invention determines transmembrane pressure TMP as follows.

Computing unit 19 of the device for determining the hematocrit first calculates, according to equation (7), longitudinal resistance $R_b$ of the dialyzer as a function of hematocrit Hkt and flow rate $Q_{tm}$ of the fluid withdrawn via membrane 2 of dialyzer 1. For this purpose, the computing unit makes use of a memory 19A, in which the parameters of the polynomial approach $\alpha_0, \alpha_1, \alpha_2, \alpha_3, \alpha_4$ are stored, which have been obtained by an offsetting calculation from individual measured data for a specific type of dialyzer. The parameters for various types of dialyzer can be stored in memory 19A of computing unit 19, whereby the computing unit then takes recourse to the parameters applicable to the type of dialyzer currently being used.

Computing unit 19 communicates with central control and computing unit 18 of the blood treatment apparatus in order to exchange the data of relevance here. For example, the computing unit may receive a data record which indicates the type of dialyzer which has previously been inputted by the user, for example by means of a keyboard. Moreover, computing unit 19 receives substitution rate $Q_{sub}$ and ultrafiltration rate $Q_{uf}$ from central control and computing unit 18, in order to calculate, from the sum of the substitution rate and the ultrafiltration rate, flow rate $Q_{tm} = Q_{sub} + Q_{uf}$ of the fluid withdrawn via membrane 2 of dialyzer 1. Furthermore, computing unit 19 receives from central control and computing unit 18 hematocrit Hkt, which can lie between 0.10 and 0.69, and total protein content TP, which can lie between 5.0 and 9.0 g/dl. Furthermore, the computing unit receives from the central control and computing unit a signal which indicates whether a pre-dilution or post-dilution is present.

According to equations (8) and (9), computing unit 19 calculates maximum flow rate $Q_{tm,max}$ from hematocrit Hkt and total protein content TP for the case where a pre-dilution or a post-dilution is carried out.

In a simplified example embodiment, longitudinal resistance $R_b$ of the dialyzer is calculated only once before or during the dialysis treatment. An improved embodiment makes provision, however, such that longitudinal resistance $R_b$ of the dialyzer is calculated at specific times in the blood treatment or is even calculated continuously during the blood treatment. The improved example embodiment proves to be particularly advantageous when one of the variables of relevance here, for example the substitution rate or ultrafiltration rate, but also the hematocrit of the patient's blood, changes during the dialysis treatment. A recalculation of longitudinal resistance $R_b$ also comes into question if a changeover is to be made from pre-dilution to post-dilution or vice versa.

A further alternative example embodiment provides for a calculation of longitudinal resistance $R_b$ not according to equation (7), but according to equation (10), which describes a general polynomial approach. In principle, however, other polynomial approaches are also possible.

A particularly preferred example embodiment makes provision such that a constant value for hematocrit Hkt, inputted for example by means of a keyboard or measured only once, is not taken as a basis. In this example embodiment, the hematocrit is continuously measured during the blood treatment by measuring unit 23. Data line 23' for transmitting the measured values for the hematocrit is represented by a broken line in FIG. 1, since the measurement of the hematocrit is not absolutely essential during the blood treatment and is provided only in the case of the particularly preferred embodiment.

During the blood treatment, moreover, as schematically shown in the method 30 of FIG. 2, pressure $P_{b,out}$ at the blood-side outlet, pressure $P_{d,in}$ at the dialysate-side inlet and pressure $P_{d,out}$ at the dialysate-side outlet are preferably measured continuously or at least at different times by means of pressure sensors 20, 21 and 22 in a step 31. Computing unit 19, which receives the measured values for the pressures via data line 20', 21', 22', calculates uncorrected transmembrane pressure $P_{TM3}$ from the pressures according to equation (3). As a further variable, computing unit 19 receives from control and computing unit 18 blood flow rate $Q_b$, which may be inputted, e.g., by the operator, in a step 32. Computing unit 19 then calculates the corrected value for transmembrane pressure $P_{TM}$=TMP according to equation (6), in a step 34, from blood flow rate $Q_D$, calculated longitudinal resistance $R_b$, of the dialyzer (determined in a step 33) and uncorrected transmembrane pressure $P_{TM3}$.

Corrected transmembrane pressure TMP may be displayed on a display unit (not shown) and/or be used for controlling or regulating the blood treatment apparatus.

The invention claimed is:

1. A method for determining the transmembrane pressure during an extracorporeal blood treatment, in which blood flows, on a blood side, at a specific blood flow rate via an arterial blood supply line of an extracorporeal blood circuit into the inlet of a first chamber of a dialyzer divided by a semipermeable membrane into the first chamber and a second chamber and flows via a venous blood return line from the outlet of the first chamber of the dialyzer, and dialyzing fluid flows, on a dialyzing fluid side, via a dialyzing fluid supply line into the inlet of the second chamber of the dialyzer and flows via a dialyzing fluid discharge line out of the outlet of the second chamber of the dialyzer, fluid being withdrawn from the blood at a specific flow rate via the membrane of the dialyzer, comprising:
    measuring the pressure on the blood side at the inlet or outlet of the first chamber of the dialyzer and on the dialyzing fluid side at the inlet and/or outlet of the second chamber of the dialyzer, or measuring the pressure on the blood side at the inlet and/or outlet of the first chamber of the dialyzer and on the dialyzing fluid side at the inlet or outlet of the second chamber of the dialyzer;
    determining a variable correlating with the viscosity of the blood;
    determining a correcting quantity for the transmembrane pressure, the correcting quantity being dependent on the variable correlating with the viscosity of the blood; and
    calculating the transmembrane pressure on the basis of the pressure measured on the blood side and the dialyzing fluid side and the correcting quantity for the transmembrane pressure.

2. The method according to claim 1, wherein the variable correlating with the viscosity of the blood is the hematocrit of the blood.

3. The method according to claim 1, wherein the variable correlating with the viscosity is continuously measured during the blood treatment.

4. The method according to claim 1, wherein the pressure on the blood side is measured in the blood return line at the outlet of the first chamber of the dialyzer and the pressure on the dialyzing fluid side is measured in the dialyzing fluid supply line at the inlet of the second chamber of the dialyzer and in the dialyzing fluid discharge line at the outlet of the second chamber of the dialyzer.

5. The method according to claim 4, wherein the transmembrane pressure is calculated from the pressure measured on the blood side and on the dialyzing fluid side and the correcting quantity according to the following equation:

$$P_{TM} = P_{TM3} + \frac{1}{2} * R_b * Q_b$$

wherein
    $R_b$ is the longitudinal resistance of the dialyzer on the blood side,
    $Q_b$ is the blood flow,
and $$P_{TM3} = P_{b,out} - \frac{P_{d,in} + P_{d,out}}{2}.$$

6. The method according to claim 1, wherein, for the determination of the correcting quantity for the transmembrane pressure, a parameter characteristic of the flow resistance of the dialyzer is determined, the parameter being dependent on the parameter correlating with the viscosity of the blood.

7. The method according to claim 6, wherein the correcting quantity is determined on the basis of the product of the parameter characteristic of the flow resistance and the blood flow rate.

8. The method according to claim 6, wherein the parameter characteristic of the flow resistance of the dialyzer is determined on the basis of the parameter correlating with the viscosity of the blood and the flow rate of the fluid withdrawn via the membrane of the dialyzer.

9. The method according to claim 8, wherein the parameter characteristic of the flow resistance of the dialyzer is calculated according to the following polynomial approach with parameters $\alpha_0, \alpha_1, \alpha_2, \alpha_3, \alpha_4$:

$$R_b(Hkt, Q_{tm}) = a_0 + a_1 * Hkt + a_2 * \frac{Q_{tm}}{Q_{tm,max}} + a_3 * Hkt * \frac{Q_{tm}}{Q_{tm,max}} + a_4 * \left(Hkt * \frac{Q_{tm}}{Q_{tm,max}}\right)^4$$

wherein
    Hkt is hematocrit,
    $Q_{tm}$ is the flow rate via the dialyzer membrane, and
    $Q_{tm,max}$ is the maximum flow rate via the dialyzer membrane.

10. A method for extracorporeal blood treatment, in which blood flows at a specific blood flow rate via an arterial blood supply line of an extracorporeal blood circuit into the inlet of a first chamber of a dialyzer divided by a semipermeable membrane into the first chamber and a second chamber and flows via a venous blood return line from the outlet of the first chamber of the dialyzer, and dialyzing fluid flows via a dialyzing fluid supply line into the inlet of the second chamber of the dialyzer and flows via a dialyzing fluid discharge line out of the outlet of the second chamber of the dialyzer, fluid being withdrawn from the blood at a specific flow rate via the membrane of the dialyzer, comprising:
    determining a transmembrane pressure comprising:
    measuring the pressure on the blood side at the inlet or outlet of the first chamber of the dialyzer and on the dialyzing fluid side at the inlet and/or outlet of the second chamber of the dialyzer, or measuring the pressure on the blood side at the inlet and/or outlet of the first chamber of the dialyzer and on the dialyzing fluid side at the inlet or outlet of the second chamber of the dialyzer;
    determining a variable correlating with the viscosity of the blood;
    determining a correcting quantity for the transmembrane pressure, the correcting quantity being dependent on the variable correlating with the viscosity of the blood; and
    calculating the transmembrane pressure on the basis of the pressure measured on the blood side and the dialyzing fluid side and the correcting quantity for the transmembrane pressure.

11. A device for determining the transmembrane pressure for a blood treatment apparatus for performing an extracorporeal blood treatment, in which blood flows, on a blood side, at a specific blood flow rate via an arterial blood supply line of an extracorporeal blood circuit into the inlet of a first chamber of a dialyzer divided by a semipermeable membrane into the first chamber and a second chamber and flows via a venous blood return line from the outlet of the first chamber of the dialyzer, and dialyzing fluid flows, on a dialyzing fluid side, via a dialyzing fluid supply line into the inlet of the second chamber of the dialyzer and flows via a dialyzing fluid discharge line out of the outlet of the second chamber of the dialyzer, fluid being withdrawn from the blood at a specific flow rate via the membrane of the dialyzer, the device comprising:
- a sensor system configured to measure the pressure on the blood side at the inlet or outlet of the first chamber of the dialyzer and on the dialyzing fluid side at the inlet and/or outlet of the second chamber of the dialyzer, or a sensor system configured to measure the pressure on the blood side at the inlet and/or outlet of the first chamber of the dialyzer and on the dialyzing fluid side at the inlet or outlet of the second chamber of the dialyzer; and
- a computing unit configured to
- determine a correcting quantity for the transmembrane pressure, said correcting quantity being dependent on a variable correlating with the viscosity of the blood, and to calculate the transmembrane pressure on the basis of the pressure measured on the blood side and dialyzing fluid side and the correcting quantity for the transmembrane pressure.

12. The device according to claim 11, wherein the variable correlating with the viscosity of the blood is the hematocrit of the blood.

13. The device according to claim 11, wherein the sensor system includes
- a sensor configured to measure the pressure in the blood discharge line at the outlet of the first chamber of the dialyzer,
- a sensor configured to measure the pressure in the dialyzing fluid supply line at the inlet of the second chamber of the dialyzer, and
- a sensor configured to measure the pressure in the dialyzing fluid discharge line at the outlet of the second chamber of the dialyzer.

14. The device according to claim 11, further comprising:
- a measuring unit configured to measure the variable correlating with the viscosity of the blood, the computing unit being configured to calculate the transmembrane pressure based on the variable which correlates with the viscosity, the variable being measured continuously during the blood treatment.

15. The device according to claim 13, wherein the computing unit is configured to calculate the transmembrane pressure from the pressure measured on the blood side, the pressure measured on the dialyzing fluid side, and the correcting quantity according to the following equation:

$$P_{TM} = P_{TM3} + \frac{1}{2} * R_b * Q_b$$

wherein
$R_b$ is the longitudinal resistance of the dialyzer on the blood side,
$Q_b$ is the blood flow, and $$P_{TM3} = P_{b,out} - \frac{P_{d,in} + P_{d,out}}{2}.$$

16. The device according to claim 11, wherein the computing unit is configured to determine the correcting quantity on the basis of the product of the parameter characteristic of the flow resistance and the blood flow rate.

17. The device according to claim 11, wherein the computing unit is configured, for the determination of the correcting quantity for the transmembrane pressure, to determine a parameter characteristic of the flow resistance of the dialyzer, the parameter characteristic of the flow resistance being dependent on the parameter correlating with the viscosity of the blood.

18. The device according to claim 17, wherein the computing unit is configured to determine the parameter characteristic of the flow resistance of the dialyzer on the basis of the parameter correlating with the viscosity of the blood and the flow rate of the fluid withdrawn via the membrane of the dialyzer.

19. The device according to claim 18, wherein the computing unit is configured to calculate the parameter characteristic of the flow resistance of the dialyzer according to the following polynomial approach with parameters $\alpha_0, \alpha_1, \alpha_2, \alpha_3, \alpha_4$:

$$R_b(Hkt, Q_{tm}) = a_0 + a_1 * Hkt + a_2 * \frac{Q_{tm}}{Q_{tm,max}} + a_3 * Hkt * \frac{Q_{tm}}{Q_{tm,max}} + a_4 \left( Hkt * \frac{Q_{tm}}{Q_{tm,max}} \right)^4$$

wherein
Hkt is hematocrit,
$Q_{tm}$ is the flow rate via the dialyzer membrane, and
$Q_{tm,max}$ is the maximum flow rate via the dialyzer membrane.

20. An apparatus for extracorporeal blood treatment comprising:
a device comprising:
- a sensor system configured to measure the pressure on the blood side at the inlet or outlet of the first chamber of the dialyzer and on the dialyzing fluid side at the inlet and/or outlet of the second chamber of the dialyzer, or a sensor system configured to measure the pressure on the blood side at the inlet and/or outlet of the first chamber of the dialyzer and on the dialyzing fluid side at the inlet or outlet of the second chamber of the dialyzer; and
- a computing unit configured to determine a correcting quantity for the transmembrane pressure, said correcting quantity being dependent on a variable correlating with the viscosity of the blood, and to calculate the transmembrane pressure on the basis of the pressure measured on the blood side and dialyzing fluid side and the correcting quantity for the transmembrane pressure.

* * * * *